United States Patent
Ini et al.

(10) Patent No.: US 7,399,871 B2
(45) Date of Patent: Jul. 15, 2008

(54) CRYSTAL FORMS OF (S)-(+)-N,N-DIMETHYL-3-(1-NAPHTHALE-NYLOXY)-3-(2-THIENYL)PROPANAMINE OXALATE AND THE PREPARATION THEREOF

(75) Inventors: Santiago Ini, Haifa (IL); Anita Liberman, Tel Aviv (IL); Tamas Koltai, Netanya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 87 days.

(21) Appl. No.: 11/371,705

(22) Filed: Mar. 8, 2006

(65) Prior Publication Data

US 2006/0270860 A1    Nov. 30, 2006

Related U.S. Application Data

(60) Provisional application No. 60/659,695, filed on Mar. 8, 2005.

(51) Int. Cl.
*C07D 333/12* (2006.01)
*C07D 333/20* (2006.01)

(52) U.S. Cl. .......................................... 549/75; 549/76

(58) Field of Classification Search ....................... None
See application file for complete search history.

(56) References Cited

U.S. PATENT DOCUMENTS 5,023,269 A * 6/1991 Robertson et al. ........... 514/438
2007/0167636 A1    7/2007 Butchko et al.

FOREIGN PATENT DOCUMENTS

| EP | 0 457 559 | 11/1991 |
|---|---|---|
| WO | WO 2004/056795 | 7/2004 |
| WO | WO 2007/077580 A2 | 7/2007 |
| WO | WO 2007/096707 A2 | 8/2007 |

OTHER PUBLICATIONS

The Merck Index 13th ed (2001), O'Neil et al. ed., Merck & Co., Inc., Whitehouse Station, NJ, p. 611, entry No. 3498.*
J. Deeter, et al., "Asymmetric Synthesis and Absolute Stereochemistry of LY248686", *Tetrahedron Letters*, vol. 31, No. 49, pp. 7101-7104, (1990).
L.A. Sorbera, et al., "Duloxetine Oxalate", *Drugs of the Future*, vol. 25, No. 9, pp. 907-916, (2000).

* cited by examiner

*Primary Examiner*—Brian J Davis
(74) *Attorney, Agent, or Firm*—Kenyon & Kenyon LLP

(57) ABSTRACT

DNT-Oxal crystalline forms and processes for making DNT-Oxal crystalline forms are provided.

15 Claims, 4 Drawing Sheets

US 7,399,871 B2

CRYSTAL FORMS OF (S)-(+)-N,N-DIMETHYL-3-(1-NAPHTHALE-NYLOXY)-3-(2-THIENYL)PROPANAMINE OXALATE AND THE PREPARATION THEREOF

CROSS REFERENCE TO RELATED APPLICATIONS

This application claims the benefit of U.S. Provisional Patent Application No. 60/659,695 filed Mar. 8, 2005, which is incorporated herein by reference.

FIELD OF THE INVENTION

The present invention is directed to crystal forms of (S)-(+)-N,N-Dimethyl-3-(1-naphthalenyloxy)-3-(2-thienyl)propanamine oxalate (DNT-Oxal) and to processes for crystallizing the crystal forms of DNT-Oxal.

BACKGROUND OF THE INVENTION

Duloxetine is a dual reuptake inhibitor of the neurotransmitters serotonin and norepinephrine. It has been found to be useful in the treatment of stress urinary incontinence (SUI), depression, and pain management. The primary raw material in the synthesis of duloxetine is (S)-(+)-N,N-Dimethyl-3-(1-naphthalenyloxy)-3-(2-thienyl)propanamine oxalate (DNT-Oxal).

The preparation of DNT-Oxal is described in European Patent Application No. EP 457,559 A3 and International Patent Application Publication WO 2004/056,795 A, as well as in Deeter, J. et al, *Tetrahedron Lett.,* 1990, 31, 7101. However, Deeter et al. fail to describe the procedure accurately, and do not disclose any crystalline form of DNT-Oxal.

Polymorphism, the occurrence of different crystal forms, is a property of some molecules and molecular complexes. A single molecule, such as DNT-Oxal, may give rise to a variety of crystalline forms having distinct crystal structures and physical properties, such as melting point, x-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids, sharing the same molecular formula, yet having distinct advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly, so that it does not accumulate in a deleterious environment. Different crystalline forms or polymorphs of the same pharmaceutical compounds can and reportedly do have different aqueous solubilities.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

There is a need in the art for the discovery of new forms of DNT-Oxal and/or processes for their preparation.

SUMMARY OF THE INVENTION

One embodiment of the invention encompasses a DNT-Oxal crystal form, characterized by X-ray powder diffraction peaks at about 6.2, 18.7, 19.8, 21.3 and 24.9 degrees two-theta, ±0.2 degrees two-theta.

Another embodiment of the invention encompasses a DNT-Oxal crystal form, characterized by X-ray powder diffraction peaks at about 6.7, 15.5, 17.6, 20.1 and 23.4 degrees two-theta, ±0.2 degrees two-theta.

Another embodiment of the invention encompasses a DNT-Oxal crystal form, characterized by X-ray powder diffraction peaks at about 6.7, 12.2, 15.6, 20.7 and 22.4 degrees two-theta, ±0.2 degrees two-theta.

Another embodiment of the invention encompasses a DNT-Oxal crystal form, characterized by X-ray powder diffraction peaks at about 6.6, 13.2, 19.8 and 23.1 degrees two-theta, ±0.2 degrees two-theta.

Another embodiment of the invention encompasses a DNT-Oxal crystal form, characterized by X-ray powder diffraction peaks at about 7.1 and 21.1 degrees two-theta, ±0.2 degrees two-theta.

Another embodiment of the invention encompasses a DNT-Oxal crystal form, characterized by X-ray powder diffraction peaks at about 6.9, 15.5, 20.9 and 23.2 degrees two-theta, ±0.2 degrees two-theta.

Another embodiment of the invention encompasses a DNT-Oxal crystal form, characterized by X-ray powder diffraction peaks at about 6.6, 15.2, 20.0, 22.8 and 26.1 degrees two-theta, ±0.2 degrees two-theta.

Another embodiment of the invention encompasses a DNT-Oxal crystal form, characterized by X-ray powder diffraction peaks at about 6.4, 19.0, 20.1, 21.6 and 25.5 degrees two-theta, ±0.2 degrees two-theta.

The present invention also provides processes for preparing the above crystalline forms of DNT-Oxal. Preferably, the crystalline forms of DNT-Oxal of the invention are polymorphically pure.

Another embodiment of the invention encompasses pharmaceutically acceptable salts of duloxetine, prepared by obtaining one of crystalline form of DNT-Oxal as described above, and converting the DNT-Oxal crystal form to pharmaceutically acceptable salts of duloxetine. Preferably, the DNT-Oxal crystal form is converted to duloxetine hydrochloride.

DETAILED DESCRIPTION OF THE INVENTION

As used herein, the term "polymorphically pure" refers to a crystal form that contains impurities in an amount of less than about 5 percent by weight, based on the total weight of the sample.

The term "impurities" is defined to include other crystal forms of DNT-Oxal. Preferably, the impurity is crystal Form II.

As used herein, "polymorphically stable" refers to a crystalline form that does not transform to other crystalline forms.

As used herein the term "room temperature" refers to the range of temperatures of from about 20° C. to about 25° C.

The present invention is directed to crystal forms of (S)-(+)-N,N-Dimethyl-3-(1-naphthalenyloxy)-3-(2-thienyl)propanamine oxalate (DNT-Oxal), processes for the preparation of the crystal forms of DNT-Oxal, and pharmaceutical compositions comprising the crystal forms of DNT-Oxal.

Figure 1:
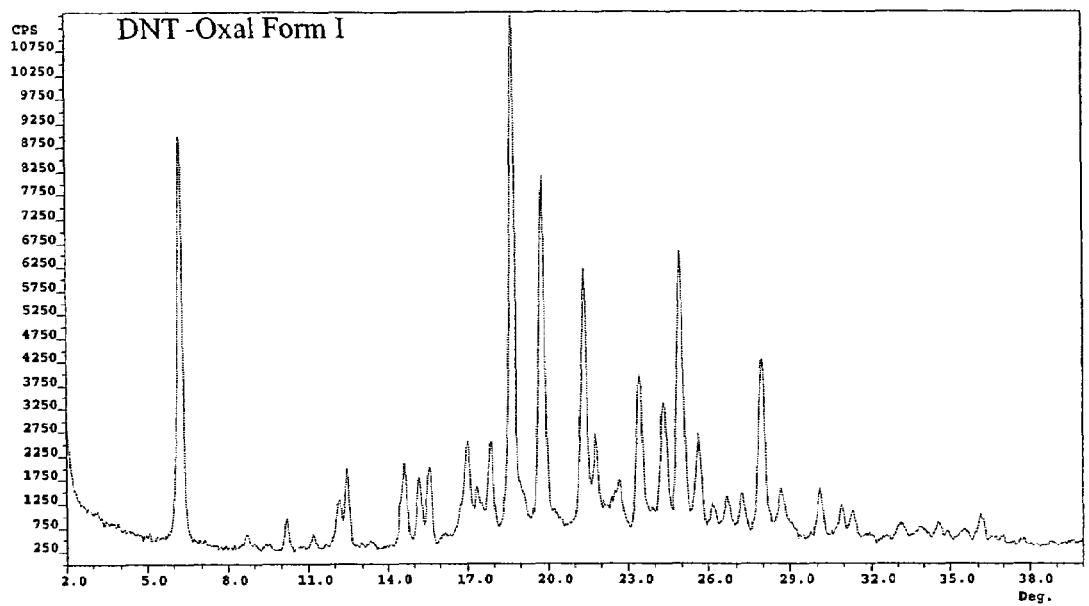
FIG. 1 illustrates the powder X-ray diffraction pattern for DNT-Oxal Form I.

One embodiment of the invention encompasses a DNT-Oxal crystalline form, characterized by X-ray powder diffraction peaks at about 6.2, 18.7, 19.8, 21.3 and 24.9 degrees two-theta, ±0.2 degrees two-theta. This form is denominated Form I. Form I may be characterized further by X-ray powder diffraction peaks at about 12.4, 15.1, 17.0, 23.4 and 24.3 degrees two-theta, ±0.2 degrees two-theta. Form I may be substantially identified by FIG. 1.

Preferably, crystals of Form I are polymorphically pure, more preferably, Form I contains less than 2% by weight, and, most preferably, less than 1% by weight, of other crystalline forms of DNT-Oxal. Specifically, these crystalline forms are either Form II or Form IV of DNT-Oxal.

Another embodiment of the invention encompasses a process for preparing DNT-Oxal crystalline Form I. The process comprises providing a slurry of DNT-Oxal crystalline Form II in methyl isobutyl ketone (MIBK), and stirring for a period of time and at temperature sufficient to form DNT-Oxal crystalline Form I. Preferably, the slurry is stirred for about 24 hours, at a temperature of from about 20° C. to about 30° C. Form II may be prepared as described below.

Another embodiment of the invention encompasses a process for preparing DNT-Oxal crystalline Form I. The process comprises providing a solution of DNT-Oxal in MIBK at the reflux temperature of the solvent, and cooling to a temperature sufficient to form crystals of DNT-Oxal crystalline Form I. Preferably, the solution is cooled to about room temperature. Preferably, prior to cooling, the solution is maintained, while stirring, for about 30 minutes.

Figure 2:
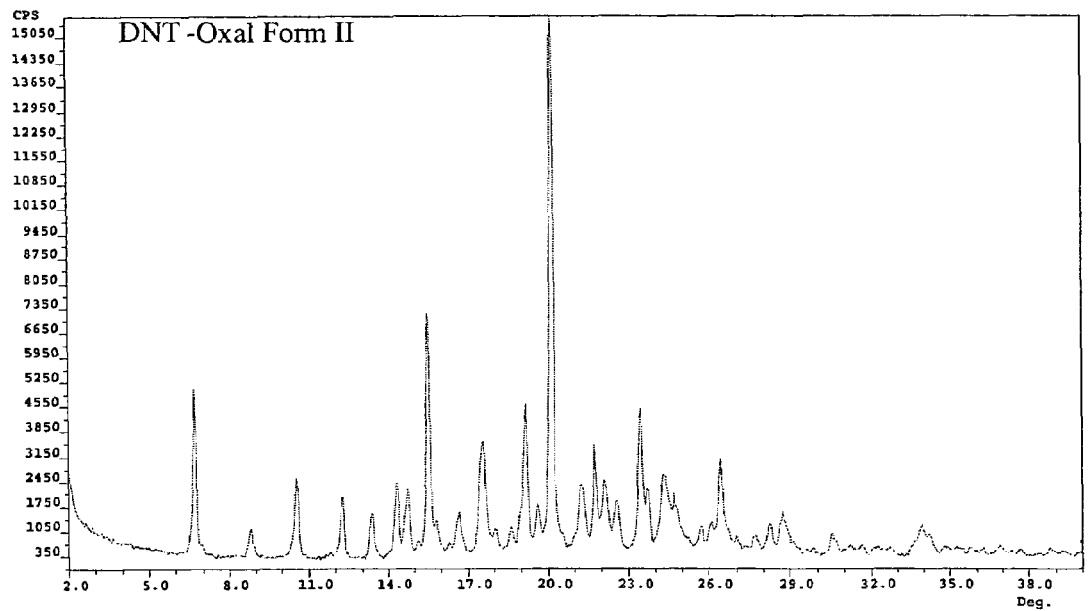
FIG. 2 illustrates the powder X-ray diffraction pattern for DNT-Oxal Form II.

Another embodiment of the invention encompasses a DNT-Oxal crystalline form, characterized by X-ray powder diffraction peaks at about 6.7, 15.5, 17.6, 20.1 and 23.4 degrees two-theta, ±0.2 degrees two-theta. This form is denominated Form II. Form II may be characterized further by X-ray powder diffraction peaks at about 10.5, 14.3, 14.7, 19.2 and 21.8 degrees two-theta, ±0.2 degrees two-theta. Form II may be substantially identified by FIG. 2.

Preferably, crystals of Form II are polymorphically pure, more preferably, Form II contains less than 2% by weight, and, most preferably, less than 1% by weight, of other crystalline forms of DNT-Oxal. Specifically, the crystalline form is Form I of DNT-Oxal Another embodiment of the invention encompasses a process for preparing Form II by drying DNT-Oxal Form I. Preferably, wet DNT-Oxal Form I is kept at a temperature of from about room temperature to about 80° C., more preferably to about 40° C., at a pressure below about 100 mm Hg in a vacuum oven, for a time sufficient to obtain DNT-Oxal Form II. As one skilled in the art will appreciate, the time required to obtain DNT-Oxal Form II will vary depending upon, among other factors, the amount of wet DNT-Oxal Form I to be dried and the drying temperature, and can be determined by taking periodic XRDs.

Another embodiment of the invention encompasses a process for preparing DNT-Oxal crystalline Form II. The process comprises providing a solution of DNT-Oxal in dimethyl formamide (DMF), and removing the DMF at a temperature and for a time sufficient to obtain DNT-Oxal crystalline Form II. Preferably, the DMF is removed by evaporating the solution to dryness under vacuum. Preferably, the solution is dried at a temperature of from about room temperature to about 70° C., more preferably, to about 60° C.

Figure 3:
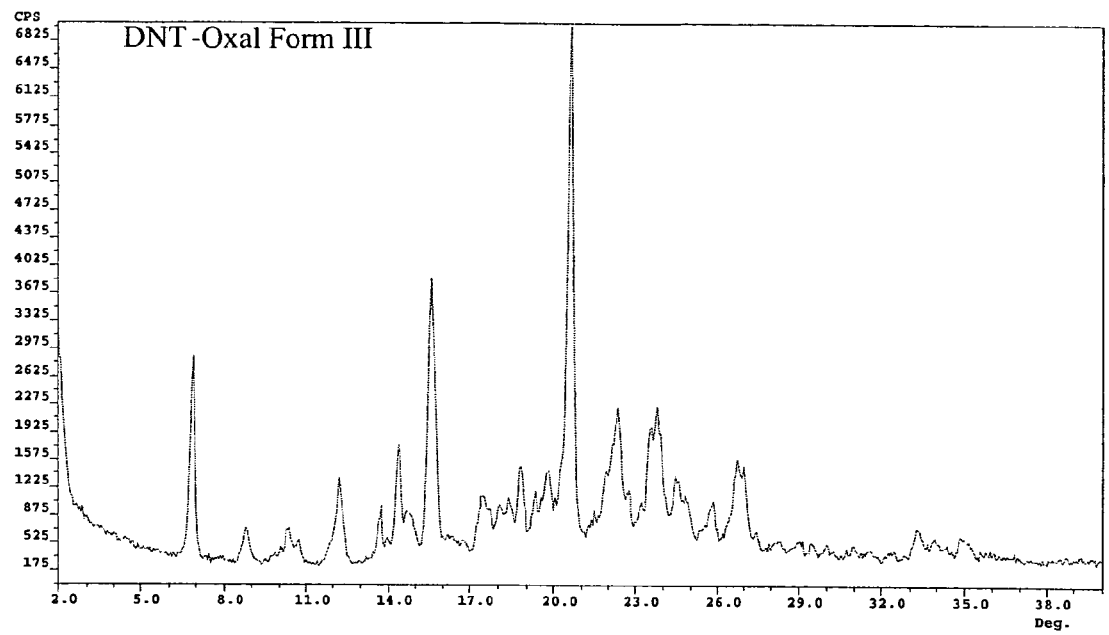
FIG. 3 illustrates the powder X-ray diffraction pattern for DNT-Oxal Form III.

Another embodiment of the invention encompasses a DNT-Oxal crystalline form, characterized by X-ray powder diffraction peaks at about 6.7, 12.2, 15.6, 20.7 and 22.4 degrees two-theta, ±0.2 degrees two-theta. This form is denominated Form III. Form III may be characterized further by X-ray powder diffraction peaks at about 14.4, 23.8 and 26.7 degrees two-theta, ±0.2 degrees two-theta. Form III may be substantially identified by FIG. 3.

Preferably, crystals of Form III are polymorphically pure, more preferably, Form III contains less than 2% by weight, and, most preferably, less than 1% by weight, of other crystalline forms of DNT-Oxal. Specifically, the crystalline form is Form II of DNT-Oxal.

Another embodiment of the invention encompasses a process for preparing DNT-Oxal crystalline Form III. The process comprises providing a solution of DNT-Oxal with methanol at the reflux temperature of the solvent, and cooling to a temperature sufficient to form crystals of DNT-Oxal crystalline Form III. Preferably, the solution is cooled to about room temperature. Preferably, prior to cooling, the solution is maintained, while stirring for about 30 minutes.

Another embodiment of the invention encompasses a process for preparing DNT-Oxal crystalline Form III. The process comprises providing a solution of DNT-Oxal with dimethyl carbonate at the reflux temperature of the solvent, and cooling to a temperature sufficient to form crystals of DNT-Oxal crystalline Form III. Preferably, the solution is cooled to about room temperature. Preferably, prior to cooling, the solution is maintained, while stirring, for about 30 minutes.

Figure 4:
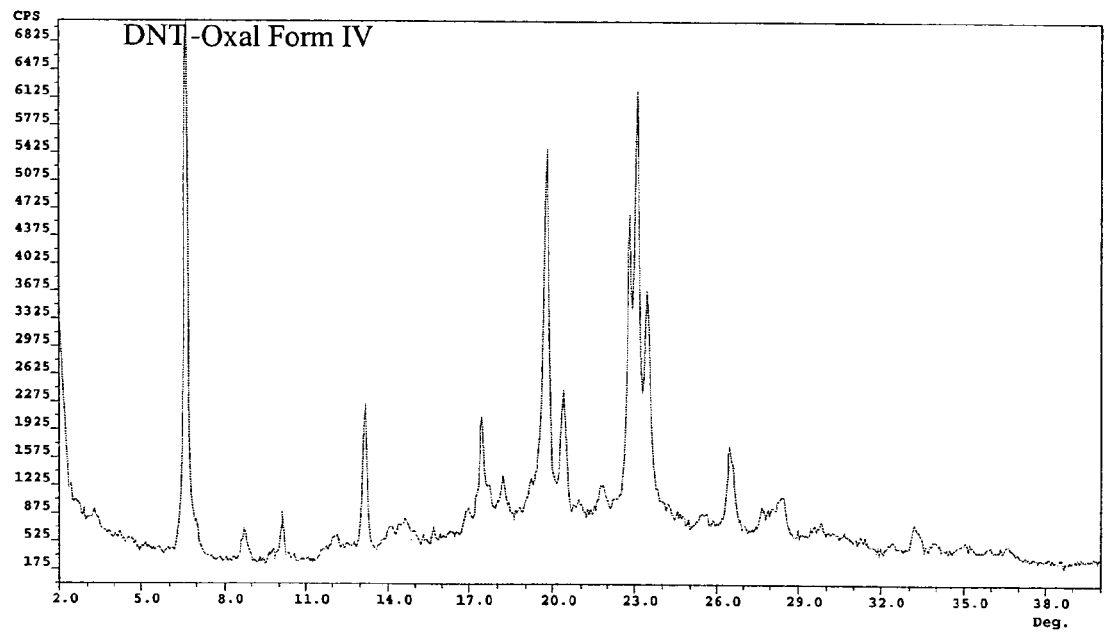
FIG. 4 illustrates the powder X-ray diffraction pattern for DNT-Oxal Form IV.

Another embodiment of the invention encompasses a DNT-Oxal crystalline form, characterized by X-ray powder diffraction peaks at about 6.6, 13.2, 19.8 and 23.1 degrees two-theta, ±0.2 degrees two-theta. This form is denominated Form IV. Form IV may be characterized further by X-ray powder diffraction peaks at about 17.4, 20.4, 22.8, 23.4 and 26.4 degrees two-theta, ±0.2 degrees two-theta. Form IV may be substantially identified by FIG. 4.

Preferably, crystals of Form IV are polymorphically pure, more preferably, Form IV contains less than 2% by weight, and, most preferably, less than 1% by weight, of other crystalline forms of DNT-Oxal. Specifically, these crystalline forms are one of Form I, Form II, Form V, or Form VIII of DNT-Oxal.

Another embodiment of the invention encompasses a process for preparing DNT-Oxal crystalline Form IV. The process comprises providing a solution of DNT-Oxal with ACN at the reflux temperature of the solvent, and cooling to a temperature sufficient to form crystals of DNT-Oxal crystalline Form IV. Preferably, the solution is cooled to about room temperature. Preferably, prior to cooling, the solution is maintained, while stirring, for about 30 minutes.

Another embodiment of the invention encompasses a process for preparing DNT-Oxal crystalline Form IV. The process comprises providing a slurry of DNT-Oxal crystalline Form II in ACN, and stirring for a period of time and at temperature sufficient to form DNT-Oxal crystalline Form IV. Preferably, the slurry is stirred for about 24 hours at a temperature of from about room temperature to about the reflux temperature of the solvent, more preferably, at a temperature of from about 20° C. to about 30° C.

Figure 5:
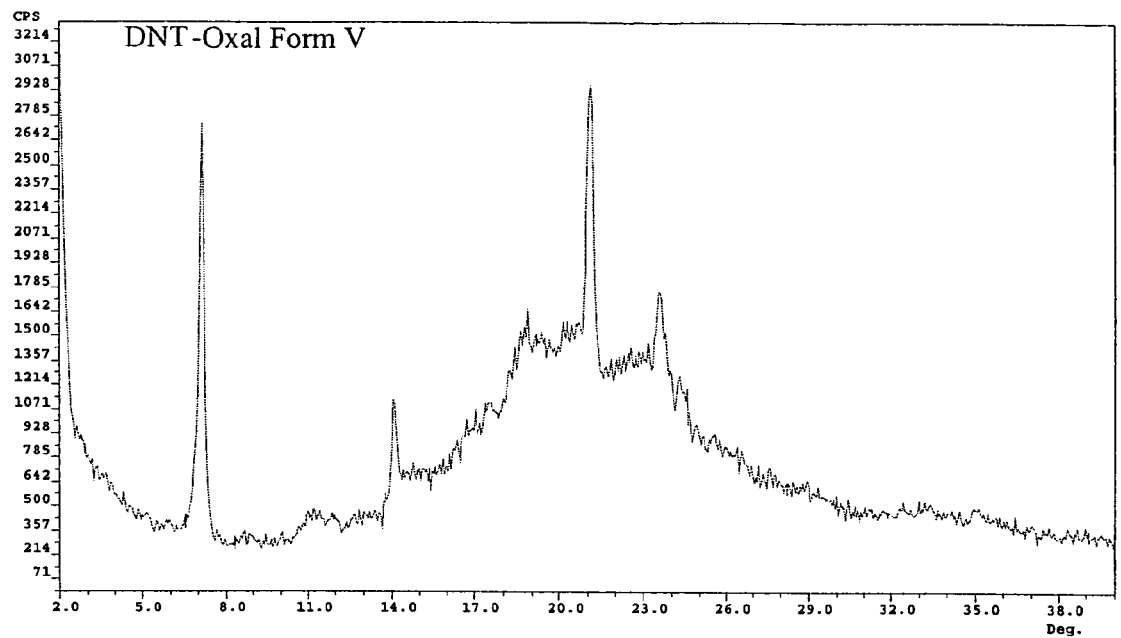
FIG. 5 illustrates the powder X-ray diffraction pattern for DNT-Oxal Form V.

Another embodiment of the invention encompasses a DNT-Oxal crystalline form, characterized by X-ray powder diffraction peaks at about 7.1 and 21.1 degrees two-theta, ±0.2 degrees two-theta. This form is denominated Form V. Form V may be characterized further by X-ray powder diffraction peaks at about 14.1 and 23.5 degrees two-theta, ±0.2 degrees two-theta. Form V may be substantially identified by FIG. 5.

Preferably, crystals of DNT-Oxal Form V are polymorphically pure, more preferably, Form V contains less than 2% by weight, and, most preferably, less than 1% by weight, of other crystalline forms of DNT-Oxal. Specifically, these crystalline forms are either Form II or Form IV of DNT-Oxal.

Another embodiment of the invention encompasses a process for preparing DNT-Oxal crystalline Form V by drying DNT-Oxal Form IV.

Preferably, wet DNT-Oxal Form IV is kept at a temperature of from about room temperature to about 70° C., more preferably to about 40° C., at a pressure below about 100 mm Hg in a vacuum oven, for a time sufficient to obtain DNT-Oxal Form V. As one skilled in the art will appreciate, the time required to obtain DNT-Oxal Form V will vary depending upon, among other factors, the amount of wet DNT-Oxal Form IV to be dried and the drying temperature, and can be determined by taking periodic XRDs.

Figure 6:
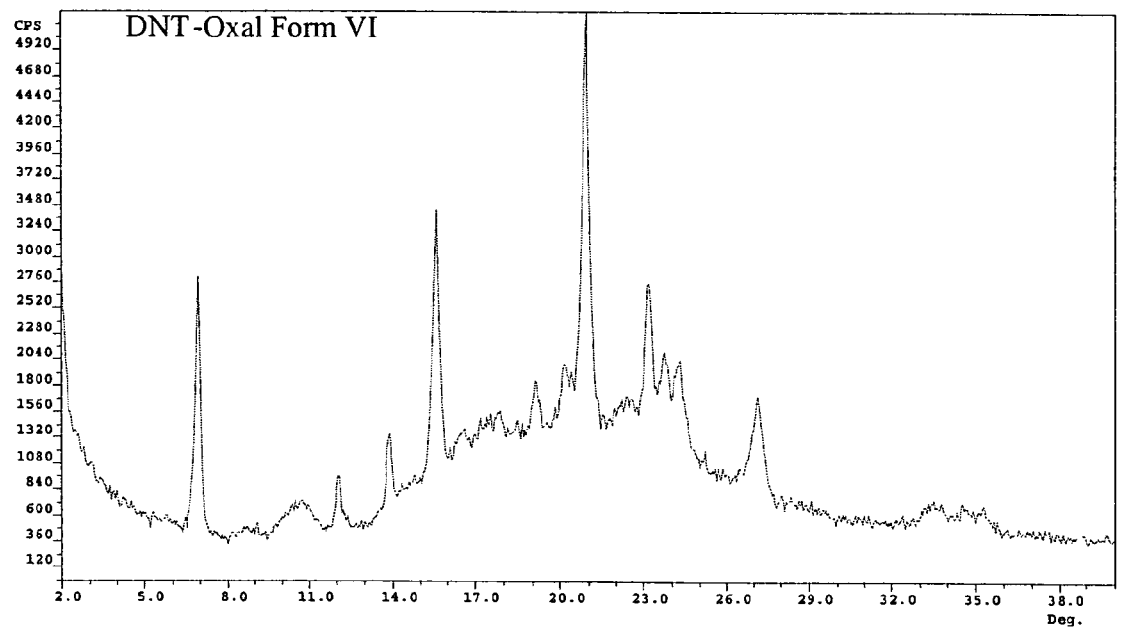
FIG. 6 illustrates the powder X-ray diffraction pattern for DNT-Oxal Form VI.

Another embodiment of the invention encompasses a DNT-Oxal crystalline form, characterized by X-ray powder diffraction peaks at about 6.9, 15.5, 20.9 and 23.2 degrees two-theta, ±0.2 degrees two-theta. This form is denominated Form VI. Form VI may be characterized further by X-ray powder diffraction peaks at about 13.9, 19.1, 23.8, 24.3 and 27.1 degrees two-theta, ±0.2 degrees two-theta. Form VI may be substantially identified by FIG. 6.

Preferably, crystals of DNT-Oxal Form VI are polymorphically pure, more preferably, Form VI contains less than 2% by weight, and, most preferably, less than 1% by weight, of other crystalline forms of DNT-Oxal. Specifically, the crystalline form is Form II of DNT-Oxal.

Another embodiment of the invention encompasses a process for preparing DNT-Oxal crystalline Form VI by drying DNT-Oxal Form VII. Form VII may be prepared as described below.

Preferably, wet DNT-Oxal Form VII is kept at a temperature of from about room temperature to about 70° C., more preferably to about 40° C., at a pressure below about 100 mm Hg in a vacuum oven, for a time sufficient to obtain DNT-Oxal Form VI. As one skilled in the art will appreciate, the time required to obtain DNT-Oxal Form VI will vary depending upon, among other factors, the amount of wet DNT-Oxal Form VII to be dried and the drying temperature, and can be determined by taking periodic XRDs.

Figure 7:
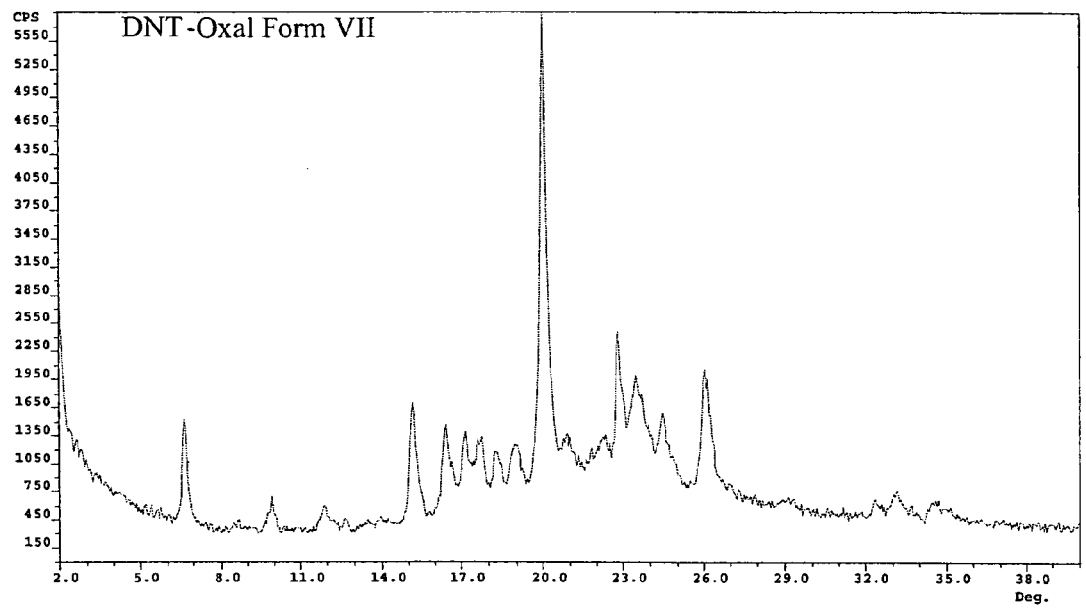
FIG. 7 illustrates the powder X-ray diffraction pattern for DNT-Oxal Form VII.

Another embodiment of the invention encompasses a DNT-Oxal crystalline form, characterized by X-ray powder diffraction peaks at about 6.6, 15.2, 20.0, 22.8 and 26.1 degrees two-theta, ±0.2 degrees two-theta. This form is denominated Form VII. Form VII may be characterized further by X-ray powder diffraction peaks at about 16.4, 17.7, 19.0 and 23.5 degrees two-theta, ±0.2 degrees two-theta. Form VII may be substantially identified by FIG. 7.

Preferably, crystals of DNT-Oxal Form VII are polymorphically pure, more preferably, Form VII contains less than 2% by weight, and, most preferably, less than 1% by weight, of other crystalline forms of DNT-Oxal. Specifically, these crystalline forms are either Form II or Form VI of DNT-Oxal.

Another embodiment of the invention encompasses a process for preparing DNT-Oxal crystalline Form VII. The process comprises providing a solution of DNT-Oxal with dichloromethane at the reflux temperature of the solvent, and cooling to a temperature sufficient to form crystals of DNT-Oxal crystalline Form VII. Preferably, the solution is cooled to about room temperature. Preferably, prior to cooling, the solution is maintained, while stirring, for about 30 minutes.

Figure 8:
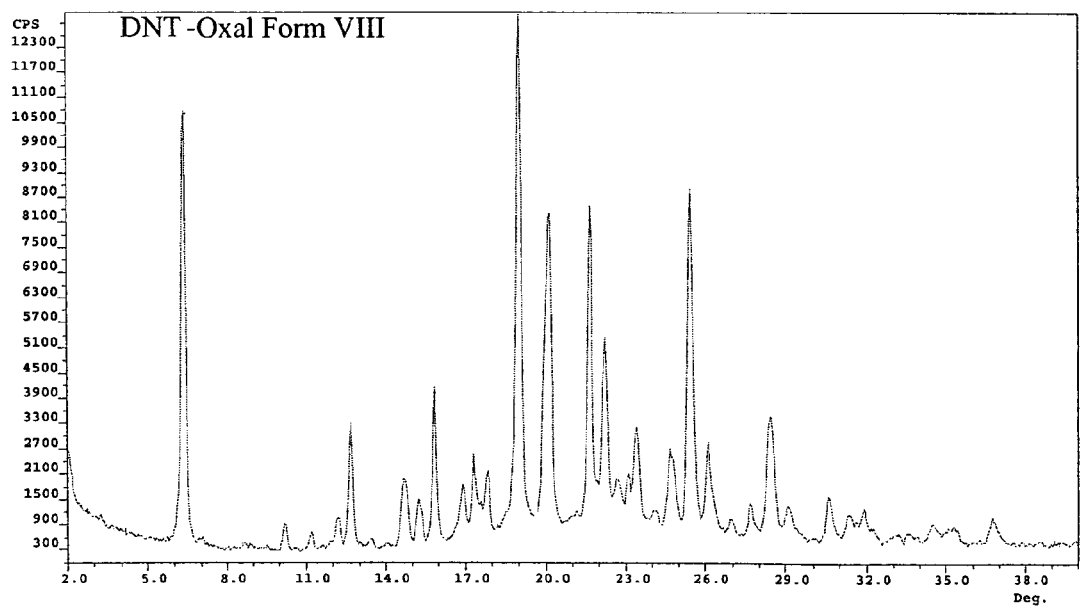
FIG. 8 illustrates the powder X-ray diffraction pattern for DNT-Oxal Form VIII.

Another embodiment of the invention encompasses a DNT-Oxal crystalline form, characterized by X-ray powder diffraction peaks at about 6.4, 19.0, 20.1, 21.6 and 25.5 degrees two-theta, ±0.2 degrees two-theta. This form is denominated Form VIII. Form VIII may be characterized further by X-ray powder diffraction peaks at about 12.7, 15.8, 22.2 and 28.5 degrees two-theta, ±0.2 degrees two-theta. Form VIII may be substantially identified by FIG. 8.

Preferably, crystals of DNT-Oxal Form VIII are polymorphically pure, more preferably, Form VIII contains less than 2% by weight, and, most preferably, less than 1% by weight, of other crystalline forms of DNT-Oxal. Specifically, these crystalline forms are one of Form II, Form IV, or Form V of DNT-Oxal.

Another embodiment of the invention encompasses a process for preparing DNT-Oxal crystalline Form VIII. The process comprises providing a slurry of DNT-Oxal crystalline Form II in dioxane, and stirring for a period of time and at temperature sufficient to form DNT-Oxal crystalline Form VIII. Preferably, the slurry is stirred for about 24 hours at a temperature of from about room temperature to about the reflux temperature of the solvent, more preferably, at a temperature of from about 20° C. to about 30° C.

Crystal forms of DNT-Oxal were stored at room temperature for 11 months. Crystal Forms II and III were found polymorphically stable.

TABLE 1

Stability results of DNT-Oxal crystal Forms II and III

| Crystal form before the storage | Crystal form after the storage |
|---|---|
| Form II | Form II |
| Form III | Form III |

Preferably, the DNT-Oxal crystal forms of the present invention have a maximum particle size of no more than about 500 μm, preferably no more than about 300 μm, and, more preferably, no more than about 200 μm. A particularly preferred form of DNT-Oxal crystal has an average particle size of no more than about 100 μm, and, most preferably, no more than about 50 μm.

The term "maximum particle size" refers to the average particle diameter, which may be measured by any of the methods commonly known in the art. The following methods, for example, may be used: sieves, sedimentation, electrozone sensing (coulter counter), microscopy, or Laser Diffraction methods.

Another embodiment of the invention encompasses pharmaceutically acceptable salts of duloxetine, prepared by obtaining one of DNT-Oxal crystal forms I, II, III, IV, V, VI, VII, or VIII as described above, and converting the DNT-Oxal crystal form to pharmaceutically acceptable salts of duloxetine. Preferably, the DNT-Oxal crystal form is converted to duloxetine hydrochloride.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

The forms of DNT-Oxal were identified using a Scintag X-ray powder diffractometer model X'TRA with a Cu-tube solid state detector. The sample holder was a round standard aluminum sample holder with rough zero background quartz plate with a cavity having a diameter of 25 mm and a depth of 0.5 mm. The scanning parameters were as follows: a range of 2° to 40° 2θ; a continuous scan mode, and a step size of 0.05° at a rate of 3°/minute.

Preparation of DNT-Oxal Crystal Forms

Preparation of DNT-Oxal Form I

Example 1

A slurry of 2 g of DNT-Oxal Form II in 10 ml of methyl isobutyl ketone (MIBK) was stirred at 20° to 30° C. for 24 hours. The solid was filtered and washed with 5 ml of the same solvent. The wet material was analyzed by XRD, and found to be Form I. After drying in a vacuum oven at 40° C. for 16 hours, a mixture of Form I and Form II (30%) was obtained.

Example 2

A 2 g sample of DNT-Oxal was combined with 5 ml MIBK, heated to reflux in an oil bath at 117° C., and additional solvent was added. Complete dissolution occurs after a total volume of 70 ml was added. After the compound was dissolved, the solution was stirred at the same temperature for half an hour, the oil bath was removed, and the solution was cooled to room temperature. The solid was filtered and washed with 5 ml of MIBK. The wet material was analyzed by XRD and found to be Form I. After drying in a vacuum oven at 40° C. for 16 hours, Form II was obtained.

Preparation of DNT-Oxal Form II

Example 3

A 2 g sample of DNT-Oxal was dissolved in 5 ml DMF and evaporated to dryness at 60° C. under vacuum. The solid was dried in a vacuum oven at 40° C. for 16 hours, and XRD demonstrates that the sample is Form II both before and after drying.

Preparation of DNT-Oxal Form III

Examples 4-5

DNT-Oxal (2 g) was combined with the appropriate solvent (5 ml), heated to reflux, and additional solvent was added until complete dissolution. After the compound was dissolved, the solution was stirred at the same temperature for half an hour, then the oil bath was removed and the solution was cooled to room temperature. The solid was filtered and washed with 5 ml of the same solvent and dried in a vacuum oven at 40° C. for 16 hours.

| Example | Solvent | Total Volume (ml) | Form before Drying | Form After Drying |
|---|---|---|---|---|
| 4 | Methanol | 10 | III | III |
| 5 | Dimethyl carbonate | 130 | III | III |

Preparation of DNT-Oxal Forms IV and V

Example 6

A 2 g sample of DNT-Oxal was combined with 5 ml of acetonitrile, heated to reflux, and additional solvent was added until the sample was completely dissolved in a total volume of 35 ml of solvent. After the compound was dissolved, the solution was stirred at the same temperature for half an hour, the oil bath was then removed, and the solution was cooled to room temperature. The solid was filtered and washed with 10 ml of acetonitrile. The wet material was analyzed by XRD and found to be Form IV. After drying in a vacuum oven at 40° C. for 16 hours, Form V was obtained.

Example 7

A slurry containing 2 g of DNT-Oxal Form II in 10 ml of ACN was stirred at 20° to 30° C. for 24 hours. The solid was filtered and washed with 7 ml of same solvent. The wet material was analyzed by XRD and found to be Form IV. After drying in a vacuum oven at 40° C. for 16 hours, a mixture of Form IV and Form V (1:1) was obtained.

Preparation of DNT-Oxal Form VI

Example 8

DNT-Oxal Form VII was heated at 40° C. in a vacuum oven for about 16 hours. The dried material was analyzed with XRD, and found to be Form VI.

Preparation of DNT-Oxal Form VII

Example 9

A 2 g sample of DNT-Oxal was combined with 5 ml of dichloromethane, and heated to reflux. Additional solvent was added until completely dissolve the sample, using a total volume of 95 ml of solvent. After the compound was dissolved, the solution was stirred at the same temperature for half an hour, the oil bath was then removed, and the solution was cooled to room temperature. The solid was filtered and washed with 5 ml of dichloromethane. The wet material was analyzed by XRD, and found to be Form VII.

Preparation of DNT-Oxal Form VIII

Example 10

A slurry of 2 g of DNT-Oxal Form II in 10 ml of dioxane was stirred at 20° to 30° C. for 24 hours. The solid was filtered and washed with 10 ml of same solvent. The wet material was analyzed by XRD, and found to be Form VIII.

Example 11

A slurry of 2 g of DNT-Oxal Form II in 10 ml of dioxane was stirred at 20° to 30° C. for 24 hours. The solid was filtered and washed with 10 ml of same solvent. The solid was filtered and washed with 5 ml of the same solvent, and dried under vacuum oven at 40° C. for 16 hours. An XRD analysis demonstrates that the dried sample was Form VIII.

Preparation of a mixture of DNT-Oxal Forms I and IV

Example 12

A slurry of 2 g of DNT-Oxal Form II in 135 ml of ethyl acetate was heated to reflux for two hours, and the solid was hot filtered at 75° C. The wet material was analyzed by XRD, and found to contain 80 percent by weight Form I and 20 percent by weight Form IV.

Example 13

A sample of DNT-Oxal containing 80 percent by weight Form I and 20 percent by weight Form IV was heated at 40° C. in a vacuum oven for about 16 hours. An XRD analysis showed that the dried sample was a 1:1 mixture of Form I and Form IV.

Comparative Example

The procedure disclosed in EP 457,559 was repeated as follows: A 2 g sample of DNT-Oxal was combined with 25 ml of methanol, and heated to 35° C. until completely dissolved. After the compound was dissolved, 25 ml of ethyl acetate was added, the oil bath was then removed, and the solution was cooled to and kept at 5° C. overnight. The solid was filtered and dried in a vacuum oven at 40° C. for 24 hours. An XRD analysis indicates that a 1:1 mixture of DNT-Oxal Form VIII and IV was formed.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed is:

1. A crystalline form of DNT-Oxal, characterized by an X-ray powder diffraction pattern having peaks at about 6.7, 15.5, 17.6, 20.1 and 23.4 degrees two-theta ±0.2 degrees two-theta.

2. The crystalline form of claim 1, further characterized by an X-ray powder diffraction pattern having peaks at about 10.5, 14.3, 14.7, 19.2 and 21.8 degrees two-theta ±0.2 degrees two-theta.

3. The crystalline form of claim 1 or claim 2, wherein the DNT-Oxal crystalline form contains less than about 5% of other crystalline forms of DNT-Oxal.

4. The crystalline form of claim 3, wherein the DNT-Oxal crystalline form contains less than about 2% of other crystalline forms of DNT-Oxal.

5. The crystalline form of claim 4, wherein the DNT-Oxal crystalline form contains less than about 1% of other crystalline forms of DNT-Oxal.

6. The crystalline form of claim 3, wherein the DNT-Oxal crystalline form contains less than about 5% of the crystalline form of DNT-Oxal characterized by an X-ray powder diffraction pattern having peaks at about 6.2, 18.7, 19.8, 21.3 and 24.9 degrees two-theta ±0.2 degrees two-theta.

7. A process for preparing the crystalline form of claim 1, comprising drying DNT-Oxal crystalline form characterized by an X-ray powder diffraction pattern having peaks at about 6.2, 18.7, 19.8, 21.3 and 24.9 degrees two-theta ±0.2 degrees two-theta.

8. The process of claim 7, wherein the dried DNT-Oxal crystalline form is kept at a temperature of from about room temperature to about 70° C.

9. The process of claim 7, wherein the dried DNT-Oxal crystalline form is kept at a temperature of about 40° C., at a pressure below about 100 mm Hg in a vacuum oven.

10. A process for preparing the form of claim 1, comprising:
   a) providing a solution of DNT-Oxal in dimethyl formamide (DMF); and
   b) removing the DMF, to form the DNT-Oxal crystalline Form of claim 1.

11. The process of claim 7 or claim 10, wherein the solution is heated to a temperature of from about 30° C. to about 70° C.

12. The process of claim 11, wherein the solution is heated to a temperature of about 60° C.

13. A crystal form of DNT-Oxal, selected from the group consisting of:
   a crystal form characterized by an X-ray powder diffraction pattern having peaks at about 6.2, 18.7, 19.8, 21.3 and 24.9 degrees two-theta, ±0.2 degrees two-theta;
   a crystal form characterized by an X-ray powder diffraction pattern having peaks at about 6.7, 12.2, 15.6, 20.7 and 22.4 degrees two-theta, ±0.2 degrees two-theta;
   a crystal form characterized by an X-ray powder diffraction pattern having peaks at about 7.1 and 21.1 degrees two-theta, ±0.2 degrees two-theta;
   a crystal form characterized by an X-ray powder diffraction pattern having peaks at about 6.9, 15.5, 20.9, and 23.2 degrees two-theta ±0.2 degrees two-theta; and
   a crystal form characterized by an X-ray powder diffraction pattern having peaks at about 6.6, 15.2, 20.0, 22.8 and 26.1 degrees two-theta ±0.2 degrees two-theta.

14. A method for preparing a DNT-Oxal crystalline form, selected from the group consisting of:
   providing a slurry of a DNT-Oxal crystalline form characterized by an X-ray powder diffraction pattern having peaks at about 6.7, 15.5, 17.6, 20.1 and 23.4 degrees two-theta ±0.2 degrees two-theta in methyl isobutyl ketone (MIBK), and stirring the slurry for a period of time and at a temperature sufficient to form a DNT-Oxal crystalline form characterized by an X-ray powder diffraction pattern having peaks at about 6.2, 18.7, 19.8, 21.3 and 24.9 degrees two-theta ±0.2 degrees two-theta;
   providing a solution of DNT-Oxal in MIBK at the reflux temperature of the solvent, and cooling the solution to a temperature sufficient to form crystals of a DNT-Oxal crystalline form characterized by an X-ray powder diffraction pattern having peaks at about 6.2, 18.7, 19.8, 21.3 and 24.9 degrees two-theta ±0.2 degrees two-theta;

providing a solution of DNT-Oxal in methanol at the reflux temperature of the solvent, and cooling the solution to a temperature sufficient to form crystals of a DNT-Oxal crystalline form characterized by an X-ray powder diffraction pattern having peaks at about 6.7, 12.2, 15.6, 20.7 and 22.4 degrees two-theta ±0.2 degrees two-theta;

providing a solution of DNT-Oxal in dimethyl carbonate at the reflux temperature of the solvent, and cooling the solution to a temperature sufficient to form crystals of a DNT-Oxal crystalline form characterized by an X-ray powder diffraction pattern having peaks at about 6.7, 12.2, 15.6, 20.7 and 22.4 degrees two-theta ±0.2 degrees two-theta;

providing a solution of DNT-Oxal in ACN at the reflux temperature of the solvent, and cooling the solution to a temperature sufficient to form crystals of a DNT-Oxal crystalline form characterized by an X-ray powder diffraction pattern having peaks at about 6.6, 13.2, 19.8 and 23.1 degrees two-theta ±0.2 degrees two-theta;

providing a slurry of a DNT-Oxal crystalline form characterized by an X-ray powder diffraction pattern having peaks at about 6.7, 15.5, 17.6, 20.1 and 23.4 degrees two-theta ±0.2 degrees two-theta in ACN, and stirring the slurry for a period of time and at temperature sufficient to form a DNT-Oxal crystalline form characterized by an X-ray powder diffraction pattern having peaks at about 6.6, 13.2, 19.8 and 23.1 degrees two-theta ±0.2 degrees two-theta;

drying a DNT-Oxal form characterized by an X-ray powder diffraction pattern having peaks at about 6.6, 13.2, 19.8 and 23.1 degrees two-theta ±0.2 degrees two-theta to obtain a DNT-Oxal crystalline form characterized by an X-ray powder diffraction pattern having peaks at about 7.1 and 21.1 degrees two-theta ±0.2 degrees two-theta;

drying a DNT-Oxal form characterized by an X-ray powder diffraction pattern having peaks at about 6.6, 15.2, 20.0, 22.8 and 26.1 degrees two-theta ±0.2 degrees two-theta to obtain a DNT-Oxal crystalline form characterized by an X-ray powder diffraction pattern having peaks at about 6.9, 15.5, 20.9 and 23.2 degrees two-theta ±0.2 degrees two-theta;

providing a solution of DNT-Oxal in dichloromethane at the reflux temperature of the solvent, and cooling the solution to a temperature sufficient to form crystals of a DNT-Oxal crystalline form characterized by an X-ray powder diffraction pattern having peaks at about 6.9, 15.5, 20.9 and 23.2 degrees two-theta ±0.2 degrees two-theta; and providing a slurry of a DNT-Oxal crystalline form characterized by an X-ray powder diffraction pattern having peaks at about 6.7, 15.5, 17.6, 20.1 and 23.4 degrees two-theta ±0.2 degrees two-theta in dioxane, and stirring the slurry for a period of time and at temperature sufficient to form a DNT-Oxal crystalline form characterized by an X-ray powder diffraction pattern having peaks at about 6.4, 19.0, 20.1, 21.6 and 25.5 degrees two-theta ±0.2 degrees two-theta.

15. A polymorphically pure crystal form of DNT-Oxal, selected from the group consisting of:

a polymorphically pure crystal form characterized by an X-ray powder diffraction pattern having peaks at about 6.6, 13.2, 19.8 and 23.1 degrees two-theta, ±0.2 degrees two-theta, which contains less than 2% by weight of other crystalline forms of DNT-Oxal; and a polymorphically pure crystal form characterized by an X-ray powder diffraction pattern having peaks at about 6.4, 19.0, 20.1, 21.6 and 25.5 degrees two-theta ±0.2 degrees two-theta, which contains less than 2% by weight of other crystalline forms of DNT-Oxal.

* * * * *